United States Patent [19]

McLaurin, Jr.

[11] Patent Number: 5,800,353
[45] Date of Patent: Sep. 1, 1998

[54] AUTOMATIC IMAGE REGISTRATION OF MAGNETIC RESONANCE IMAGING SCANS FOR LOCALIZATION, 3-DIMENSIONAL TREATMENT PLANNING, AND RADIATION TREATMENT OF ABNORMAL LESIONS

[76] Inventor: Robert L. McLaurin, Jr., 1528 Iredell Dr., Raleigh, N.C. 27608

[21] Appl. No.: 872,103

[22] Filed: Jun. 10, 1997

Related U.S. Application Data

[63] Continuation of Ser. No. 599,850, Feb. 12, 1996, abandoned.

[51] Int. Cl.$^6$ ............................................. A61B 5/055
[52] U.S. Cl. ........................ 600/407; 600/417; 600/436
[58] Field of Search .......................... 600/407, 414, 600/417, 421, 436, 410; 128/920; 606/130; 378/205, 206, 64, 65

[56] References Cited

U.S. PATENT DOCUMENTS

| | | |
|---|---|---|
| 4,651,732 | 3/1987 | Frederick . |
| 4,923,459 | 5/1990 | Nambu . |
| 5,107,839 | 4/1992 | Houdek et al. . |
| 5,207,223 | 5/1993 | Adler . |
| 5,285,787 | 2/1994 | Machida . |
| 5,501,218 | 3/1996 | Usui . |
| 5,553,112 | 9/1996 | Hardy et al. . |
| 5,682,890 | 11/1997 | Kormos et al. . |

OTHER PUBLICATIONS

Grimson et al. "Automation Registration for Enhanced Reality Visualization in Surgery", Sep. 1995.

*Primary Examiner*—Marvin M. Lateef
*Assistant Examiner*—Shawna J. Shaw
*Attorney, Agent, or Firm*—Mills Law Firm PLLC; Clifford F. Rey

[57] ABSTRACT

This invention is a method of using the Magnet Center of a magnetic resonance imaging scanner, commonly referred to as MRI, as the common reference point to accurately film image an area of concern for parallel axial, sagittal and coronal parallel slices. The perpendicular axis of each of the parallel slices of film images from all three of the mutually perpendicular slices passes through Magnet Center of the MRI. Upon determination of the number of film image slices in each stack, the position of the first slice with respect to Magnet Center, and the thickness of each slice has been determined, this data is entered into a computer capable of producing three-dimensional images. Using the entered data and positioning lasers, the original position during scanning can be accurately reproduced in the simulator suite or room as well as in the Treatment room.

7 Claims, 1 Drawing Sheet

AUTOMATIC IMAGE REGISTRATION OF MAGNETIC RESONANCE IMAGING SCANS FOR LOCALIZATION, 3-DIMENSIONAL TREATMENT PLANNING, AND RADIATION TREATMENT OF ABNORMAL LESIONS

This is a Continuation In Part of application Ser. No. 08/599,850 filed on Feb. 12, 1996 entitled AUTOMATIC IMAGE REGISTRATION OF MAGNETIC RESONANCE IMAGING SCANS FOR LOCALIZATION OF RADIATION TREATMENT OF ABNORMAL LESIONS, abandoned.

FIELD OF INVENTION

This invention relates to medical procedures and, more particularly, to the Localization, Treatment Planning, Simulation and Treatment of abnormal lesions.

BACKGROUND OF INVENTION

Magnetic resonance imaging, commonly known as MRI, is superior to computerized tomography commonly referred to as CT, for providing non-invasive visualization of internal anatomic structures. First, MRI scans provide higher quality definition of the anatomy and better differentiation between normal and abnormal tissue. Secondly, MRI images can be obtained in all three standard views; i.e. front view, side view and cross-section (anatomically designated coronal, sagittal and axial views respectively). These three views significantly improve the ability of the physician to develop a 3-dimensional comprehension of the inter-relation of structures which improves diagnostic interpretation as well as therapeutic intervention. CT scans can only be obtained in one view, the axial view, or a tilted variation thereof.

Radiation therapy is the treatment of malignant tissue or abnormal lesions through the use of radiation. The guiding principle is that the malignant tissue has a diminished capacity to repair radiation damage whereas normal healthy tissue retains the ability to recover from radiation exposure. A good background discussion of radiation oncology is given in U.S. Pat. No. 5,370,117 entitled Immobilization System for Repeated Use in Imaging and Treating of Brain Tumors issued to Robert L. McLaurin, Jr. on Dec. 6, 1994.

In order to focus radiation treatment precisely on an abnormal lesion in the brain or other parts of the body, special pictures must first be taken with either CT or MRI so the target can be visualized. The patient must be immobilized so that the exact same position can be established during treatment as it was during imaging. Although MRI scans provide superior visualization as described above, they contain inherent distortion, particularly toward the edges of the image. CT scans, on the other hand, are geographically accurate and (contain almost no distortion. It is because of the geographic accuracy of CT scans that other 3-dimensional treatment planning systems and stereotactic treatment systems are based upon CT scanning and rely on external fiducial markers to provide a frame-of-reference.

When this approach is wed with MRI the apparent position of the external fiducial markers becomes distorted. Since the position of the target lesion is supposed to be defined with respect to the external markers, it has been demonstrated that the distortion of the external fiducial markers introduces an unacceptable level of inaccuracy thus rendering the direct use of MRI images unreliable for 3-D Treatment Planning or Stereotactic Treatment.

Sophisticated solutions have been developed to circumvent the above mentioned problem including Image Fusion Techniques. This technique is described in detail in an article entitled IMAGE FUSION FOR STEREOTACTIC RADIOTHERAPY AND RADIOSURGERY TREATMENT PLANNING published by the Harvard Medical School in Int. J. Radiation Oncology Biol. Phys., Vol. 28, No. 5, PP1229–1234 in 1994.

The goal of image fusion is to couple the inherent geographic accuracy of CT with the superior diagnostic quality of information provided by MRI. Basically, this is accomplished by generating a surface contour from each of the scan sets and "fitting" the surfaces together as closely as possible. Image fusion techniques are laborious and time consuming. The process of assuring that the information contained in one scan set is properly aligned with information in another scan set is called image registration.

Magnetic Resonance Imaging or MRI uses magnetic fields to produce the images. The term "Magnet Center" designates the exact physical center of the magnetic field as measured in all three dimensions. At this point in space, the linearity or straightness of the magnetic field is maximal and the fidelity or positional accuracy of the image is optimal. Because of these inherent characteristics of MRI imaging, positional accuracy is highest at Magnet Center.

External fiducial markers placed on the surface of the skin or further out have traditionally been used to establish a three dimensional coordinate system. Since the MRI scanners are designed to place the center of the body near Magnet Center, external fiducial markers are necessarily located at a distance from Magnet Center. Their peripheral location contributes to the unacceptable level of distortion which has previously nullified the use of MRI images for Treatment Planning purposes as discussed above.

The method described herein entails the use of Magnet Center as the origin of a 3-dimensional coordinate system. This technique represents a significant change from the traditional reliance upon external fiducial markers. By identifying Magnet Center precisely, the image distortion problem inherent in external fiducial markers is eliminated. Furthermore, by maintaining the Magnet Center at origin in all three standard views, the images from each view are necessarily forced into proper 3-dimensional alignment with the images from the other views. The resulting accurate alignment of scan sets from different views constitutes Automatic Image Registration. Automatic Image Registration allows for precise 3-dimensional treatment planning without the companion CT scans or Image Fusion Technique. Thus, Automatic Image Registration is highly accurate and facilitates radiation treatment delivery with stereotactic precision.

CONCISE EXPLANATION OF REFERENCES

U.S. Pat. No. 5,370,117 to Robert L. McLaurin, Jr. discloses an immobilization system for repeated use in imaging and treating of brain tumors. Although this patent envisions using MRI technology to locate and repeatedly irradiate tumors, it is admitted that there is image distortion and there is no inference to using the Magnet Center as a reference point. In other words, this patent is primarily an immobilization system for repeated use in imaging and radiation therapy.

IMAGE FUSION FOR STEREOTACTIC RADIOTHERAPY AND RADIOSURGERY TREATMENT PLANNING article published by the Harvard Medical School in Int. J. Radiation Oncology Biol. Phys., Vol. 28, No. 5, PP1229–1234 in 1994, as mentioned above, relates to vary laborious and time consuming image fusion techniques

3 which essentially are overlays of MRI images over the more accurate CT images

BRIEF DESCRIPTION OF INVENTION

In the present invention, the so-called Magnet Center of the MRI scanner is used as a reference point during imaging so the same can be reproduced for Treatment Planning, Simulation and Treatment thereby eliminating the need for CT scans or image fusion techniques.

To accomplish the above, the technician operating the MRI scanner positions the exact center of each MRI image at Magnet Center as defined above. This accurately defines the location of the anatomical target with respect to left-right, anterior-posterior and head-foot which are the three perpendicular planes of view that intersect at a single point, i.e., the Magnet Center of the MRI.

When the brain is involved, using the patented McLaurin immobilization system, the lesion, tumor or the like can be accurately located and subsequently irradiated or otherwise treated.

In view of the above, it is an object of the present invention to provide an accurate method of 3-dimensional localization of abnormalities in the body of a patient using solely an MRI scanner.

Another object of the present invention is to utilize the Magnet Center of an MRI scanner as the sole reference point for localization, Treatment Planning and Treatment of abnormalities in a patient.

Another object of the present invention is to use the Magnet Center of MRI scans as reference point for 3-Dimensional Treatment Planning.

Another object of the present invention is to use the Magnet Center as a common reference point for the standard axial, sagittal and coronal views which are mutually perpendicular.

Other objects and advantages of the present invention will become apparent and obvious from a study of the following description and the accompanying drawings which are merely illustrative of such invention.

DETAILED DESCRIPTION OF INVENTION

Figure 1:
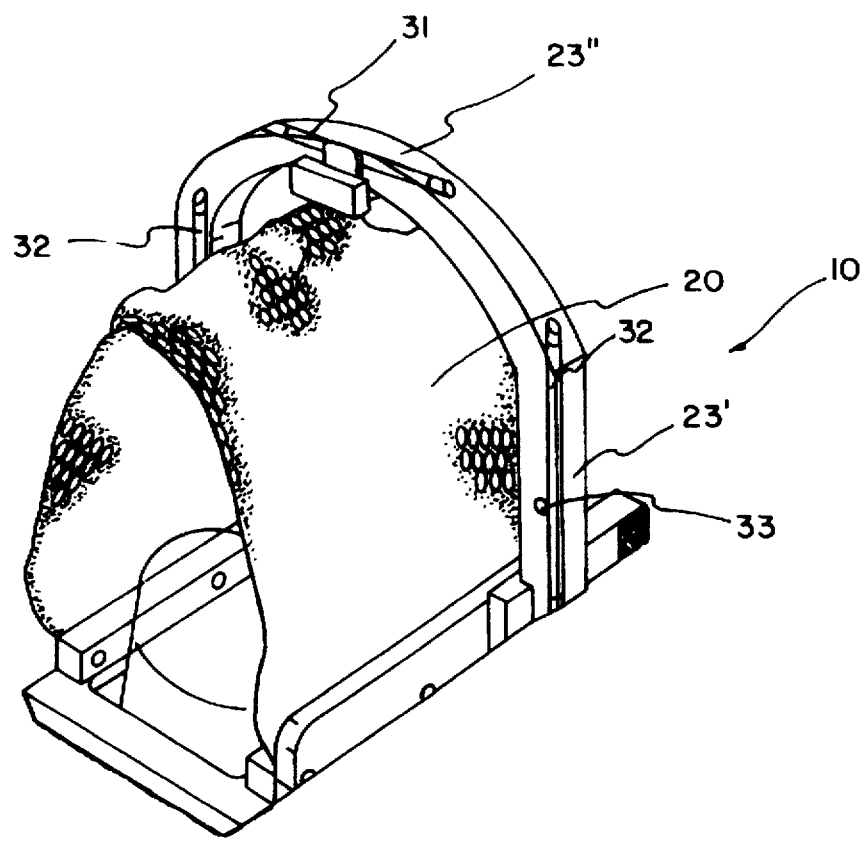
FIG. 1 is a perspective view of the McLaurin immobilization system which is compatible with MRI scanners and has contrasting portions so that X, Y and Z axis can be located and relocated on the patient.

In the method of the present invention, the Magnet Center of the MRI is used as the common reference point during imaging and is reproduced for Treatment Planning, Simulation and Treatment. For purposes of this application, the term "Magnet Center" is defined as the exact physical center of the magnetic field that is generated by the MRI scanner as measured in three dimensions.

Since MRI or magnetic resonance imaging is well known to those skilled in the art as are Treatment Planning, Simulation and Treatment, further detailed discussion of the same is not deemed necessary.

MRI scanners have a built-in frame-of-reference. This is utilized to define the location of the area of interest in a patient with respect to left-right, anterior-posterior and head-foot. The default setting for the reference point is usually at Magnet Center.

The technician operating the MRI scanner has the capability to shift the position of the reference point to focus in on a particular region of interest. When the scans will be used for Treatment Planning purposes, it is critical that the reference point remain at or as close as possible to Magnet Center so that it can be accurately reproduced in subsequent simulation and treatment procedures.

MRI scans are typically obtained in three standard views or series of parallel slices, namely, axial, sagittal and coronal views. In the present invention, these three views are all mutually perpendicular and each slice is aligned on an axis that is always at the center of the images and all three axes intersect at the Magnet Center of the MRI scanner.

On some MRI scanners, the operating technician has the capability to obtain slices at oblique angles. For scans which are to be used for Treatment Planning, however, the three standard mutually perpendicular views are required.

In Treatment Planning, the image data from the MRI scanner is transferred to a Treatment Planning system which includes a computer capable of performing radiation dose calculations with a 3-dimensional volume. In this process, the image data must be entered in a specific format so that the different views will line up correctly with respect to each other. A complete set of images in a given view is termed a "stack."

In order to provide the correct position of each image or slice in 3-dimensional space, the following parameters must be defined: 1) the number of slices in the stack; 2) the position of the first slice with respect to Magnet Center, i.e., the number of centimeters above or below, etc.; 3) the thickness of each slice; and 4) the proper magnification factor. These four parameters are on each individual image and can usually be read off the films. This standard information is routinely entered with the actual digital image for three-dimensional Treatment Planning.

In order for the three different image stacks to line up properly with respect to each other, i.e., "register" correctly, one additional piece of information must be provided during data entry. As mentioned above, there exists an axis which is perpendicular to the plane of each image that passes through magnet center. If the exact location of this line is defined on every image in each stack, then the three perpendicular axes will intersect at Magnet Center forming the origin of a true three-dimensional coordinate system. Each pixel in each digital image in each stack will then have a discreet set of coordinates with respect to the origin at Magnet Center.

Specifying the exact location of the perpendicular axis on each image is the key to the automatic image registration of the present invention.

It has been discovered that the position of the axis through Magnet Center is the same for all MRI scanners tested because of a de facto standard that exists in the community of MRI manufacturers and vendors. Each image consists of a matrix of 256×256 pixels. When the imaging parameters are maintained during imaging as described above, then the location of the perpendicular axis which passes through Magnet Center is automatically placed in the exact center of each image, i.e., at pixel coordinates 127, 127.

In the data entry procedure, the position of the perpendicular axis is designated in each of the three stacks. When this is done, the images automatically register which means they are in correct alignment and in proper relative position.

As a practical matter, the MRI scanner is usually in a separate location from the simulator and radiation treatment machines. In order to make use of the MRI images for Treatment, it is necessary to reproduce Magnet Center reference point and, therefore the frame-of-reference during Simulation and again during each treatment of the patient.

MRI scanners typically include a set of laser lights which are oriented toward Magnet Center at a known distance therefrom. These lights are used by the technologist to set the patient up prior to scanning so that the region of interest is nearest the Magnet Center. A separate set of such positioning lasers exists in the Simulator and Treatment apparatus.

An immobilization system of the type disclosed in U.S. Pat. No. 5,370,117 may be utilized to accurately reproduce the original frame-of-reference for subsequent use during Simulation and Treatment procedures. The patented immobilization system 10 shown in FIG. 1 includes an arch 23 with a contrast column 31 drilled horizontally across the apex 23" of such arch. A vertical contrast column 32 is drilled in each of the legs 23' of arch 23. Finally, a horizontal contrast column 33 is drilled through the central portion of each of the vertical legs 23. Each of these are columns 31, 32 and 33 are filled with a contrasting liquid such as oil and are sealed at their ends and are used for alignment purposes in both the MRI, the Simulator room and in the Treatment room.

The immobilizing mask 20 is secured to the arch 23 as described in U.S. Pat. No. 5,370,117. In view of this, further detailed discussion of the same is not deemed necessary.

From the above, the original position during scanning can be accurately reproduced in the Simulator suite by precise alignment with the positioning lasers which are routinely present in both Simulator and Treatment rooms. This provides the frame-of-reference within which necessary positional trans-location can be performed in accordance with the final Treatment Plan.

After final adjustments are made during Simulation, they can be reproduced for Treatment, again by way of a standard set of alignment lasers which exist expressly for the purpose of securing accurate repositioning of the patient during repeated treatment sessions.

The terms "horizontal," "vertical," "transverse," etc. have been used herein merely for convenience to describe the invention and its parts as oriented in the drawings. It is understood, however, that these terms are no way limiting to the invention since the invention may obviously be disposed in different orientations when in use.

The present invention may, of course, be carried out in other specific ways than those herein set forth without departing from the spirit and essential characteristics of such invention. The present embodiments are, therefore, to be considered in all respects as illustrative and not restrictive, and all changes coming within the meaning and equivalency range of the appended claims are intended to be embraced therein.

What is claimed is:

1. A method of automatic image registration of standard axial, coronal, and sagittal magnetic resonance images obtained by a Magnetic Resonance Imaging scanner capable of generating a magnetic field, said magnetic field having a center point defining a magnetic center which functions as the origin of a three dimensional coordinate system for locating anatomical targets in a patient for radiation treatment, said method comprising the steps of:

positioning said patient within said scanner such that an anatomical target to be visualized is located as close as possible to said magnet center;

obtaining a series of standard axial, coronal, and sagittal magnetic resonance images of said target, each of said images within said series representing a parallel image slice through said target at a predetermined interval from said magnet center, each of said image slices having a perpendicular axis extending through said magnet center; and entering digital data corresponding to said images into a computerized Treatment Planning System in a specific format including the number of image slices in each of said series, the position of a first image slice in each of said series relative to said magnet center, the thickness of each of said image slices, and the exact position of said axes extending through said magnet center such that each of said series of axial, coronal and sagittal images are aligned with respect to said magnet center and to each other enabling said series of images to be automatically registered within said three dimensional coordinate system for subsequent treatment planning and radiation therapy.

2. The method of claim 1 wherein the step of positioning is carried out by laser beam means.

3. The method of claim 1 wherein the step of positioning further includes the step of immobilizing said patient by use of an immobilization means.

4. The method claim 1 wherein the step of entering further includes the step of reproducing said coordinate system in a simulation apparatus to simulate treatment of said patient prior to actual radiation therapy.

5. The method of claim 4 wherein step of reproducing is carried by a laser beam means integrated with said simulation apparatus.

6. The method of claim 4 wherein the step of reproducing further includes the step of resetting said coordinate system in a radiation therapy apparatus in order to accurately administer a dosage of radiation to said anatomical target.

7. The method of claim 6 wherein the step of resetting is carried out by a laser beam means integrated with said radiation therapy apparatus.

* * * * *

UNITED STATES PATENT AND TRADEMARK OFFICE
CERTIFICATE OF CORRECTION

PATENT NO.   :   5,800,353
DATED        :   September 1, 1998
INVENTOR(S)  :   Robert L. McLaurin, Jr..

It is certified that error appears in the above-identified patent and that said Letters Patent is hereby corrected as shown below:

On the Title page, delete the Abstract in its entirety and substitute therefor:

ABSTRACT OF THE DISCLOSURE

This invention is a method of using the Magnet Center of a magnetic resonance imaging scanner, commonly referred to as MRI, as the common reference point to accurately image an anatomical target in axial, sagittal and coronal views and to cause the images from these three views to be accurately aligned with respect to each other in 3-Dimensional space so that they can be used for the purpose of 3-Dimensional Treatment Planning, Simulation, and Treatment of a patient. The perpendicular axis of each of the parallel images from all three of the mutually perpendicular views passes through Magnet Center of the MRI. Upon determination of the number of images in each image set, the position of the first image with respect to magnet center, and the thickness of each image, this data is entered into a 3-Dimensional Treatment Planning Computer. The entered data is then utilized to develop a 3-Dimensional Treatment Plan. Using positioning lasers, the original frame of reference established during scanning can be accurately reproduced during subsequent simulation and actual radiation treatment of a patient thereby allowing the 3-Dimensional Plan to be implemented with a high degree of accuracy.

Signed and Sealed this

Twelfth Day of January, 1999

Attest:

*Attesting Officer*           *Acting Commissioner of Patents and Trademarks*